United States Patent [19]

D'Sidocky et al.

[11] Patent Number: 4,463,191

[45] Date of Patent: Jul. 31, 1984

[54] PROCESS FOR THE REDUCTIVE ALKYLATION OF AROMATIC NITRO-CONTAINING COMPOUNDS WITH KETONES OR ALDEHYDES

[75] Inventors: Richard M. D'Sidocky, Ravenna; Dane K. Parker, Massillon, both of Ohio

[73] Assignee: The Goodyear Tire & Rubber Company, Akron, Ohio

[21] Appl. No.: 535,515

[22] Filed: Sep. 26, 1983

[51] Int. Cl.$^3$ .............................................. C07C 85/08
[52] U.S. Cl. .................................. 564/398; 564/373; 564/384; 564/392; 548/300; 549/351
[58] Field of Search ............... 564/398, 373, 384, 392; 548/300; 549/351

[56] References Cited

U.S. PATENT DOCUMENTS

| | | | |
|---|---|---|---|
| 3,336,386 | 8/1967 | Dovell et al. | 564/398 |
| 3,350,449 | 10/1967 | Wheeler | 564/398 X |
| 3,398,193 | 8/1968 | Wheeler | 564/398 X |
| 3,522,309 | 7/1970 | Kirby | 564/398 |
| 4,210,602 | 7/1980 | Bergfeld et al. | 564/398 |

*Primary Examiner*—Paul F. Shaver
*Attorney, Agent, or Firm*—D. O. Nickey

[57] ABSTRACT

There is disclosed a process for the reductive alkylation of aromatic nitro-containing compounds with ketones or aldehydes wherein the improvement is characterized in that a specific polymer bound co-catalyst system is utilized. More specifically, a polymer bound anthranilic acid palladium complex is used in conjunction with a bound sulfonic acid resin as a catalyst system in a reaction to produce compounds such as N-phenyl-N'-alkyl-p-phenylenediamine.

6 Claims, No Drawings

PROCESS FOR THE REDUCTIVE ALKYLATION OF AROMATIC NITRO-CONTAINING COMPOUNDS WITH KETONES OR ALDEHYDES

TECHNICAL FIELD

The present invention is concerned with a polymer bound catalyst system used to prepare compounds such as N-phenyl-N'-alkyl-p-phenylenediamines wherein the catalyst system overcomes numerous disadvantages presently found in the production of such compounds.

BACKGROUND ART

This invention is concerned with a process for the reductive alkylation of aromatic nitro-containing compounds with ketones or aldehydes. More specifically, this invention relates to an improvement in the synthesis of N-phenyl-N'-alkyl-p-phenylenediamines which are useful as rubber antioxidants and antiozonants. At present N-phenyl-N'-alkyl phenylenediamines are produced from p-nitrodiphenylamines which are reduced and then alkylated. Other processes for the production of p-nitrodiphenylamines are described in U.K. Pat. Nos. 798,148 and 834,510; German Pat. No. 185,663; U.S. Pat. Nos. 3,155,727 and 4,155,936. P-nitrodiphenylamine has the generic formula:

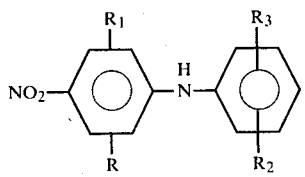

wherein R and $R_1$ are selected from the group consisting of hydrogen radicals and alkyl radicals of 1 to 9 carbon atoms; $R_2$ and $R_3$ are selected from the group consisting of hydrogen radicals, alkyl radicals from 1 to 9 carbon atoms, alkoxy radicals of 1 to 9 carbon atoms and cycloalkyl radicals of 5 to 6 carbon atoms.

Presently, p-nitrodiphenylamines are synthesized by reacting (1) para-halonitrobenzenes conforming to the following structural formula:

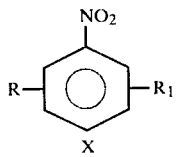

wherein X is a halogen selected from the group consisting of chlorine and bromine; and wherein R and $R_1$ are defined above; (2) with a primary aromatic amine of the following structural formula:

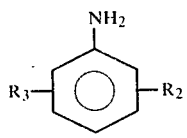

wherein $R_2$ and $R_3$ are defined as above; (3) in the presence of a neutralizing agent, selected from the group consisting of alkali metal salts, oxides of alkali metal salts and alkali metal hydroxides; (4) in the presence of a catalyst in a concentration of at least 0.1 parts by weight per hundred parts per weight of the para-halonitrobenzene; (5) at a temperature of 170°–250° C.; (6) at a pressure of from atmospheric to about 3000 kPa (kilopascals) and (7) with an excess of primary aromatic amines of from 3 to 300 percent.

Stage I of the reaction is the formation of the 4-nitrodiphenylamine. Stage II involves the reduction to 4-aminodiphenylamine while Stage III is the reductive alkylation to provide the final product.

The current Stage II commercial reaction involves the reduction of 4-nitrodiphenylamine to 4-aminodiphenylamine with a copper chromite catalyst at about 200° C.

Stage II

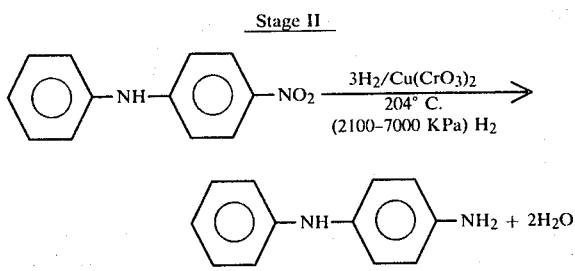

Stage III is the alkylation of 4-aminodiphenylamine with MIBK (methylisobutyl ketone) at 185° C. using a nickel catalyst which produces N-phenyl-N'-alkyl-p-phenylenediamine.

Stage III

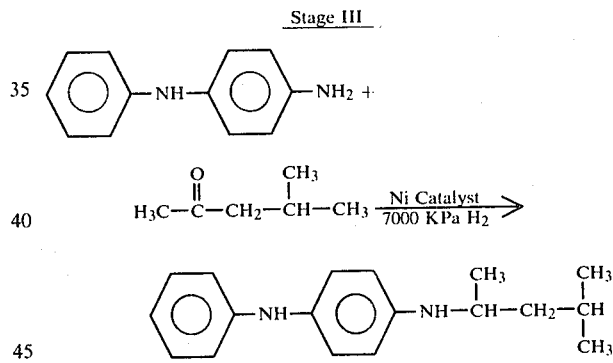

These presently accepted means of synthesis are usually conducted at temperatures lower than 205° C. and at times in excess of 12 hours. Further, the presently accepted commercial synthesis route suffers from poor product quality in that a fair amount of tars and by-products are present in the final product and the requirement of three reaction stages. The improvement of the present application is characterized in that a polymer bound anthranilic acid-palladium complex plus a bound sulfonic acid resin are used as catalysts in a combined Stage II and III reaction.

To one skilled in the art it would be apparent that the catalyst system of the present invention would be useful for the preparation of numerous compounds.

U.S. Pat. No. 4,155,936 is herein incorporated by reference and made a part hereof. Specifically, U.S. Pat. No. 4,155,936 is concerned with the incorporation of solubilizing agents in the reaction mixture to reduce reaction times and improve yields of Stage I.

The present invention provides a solution to the problems of long reaction times, limited number of suitable catalysts, environmentally unsound effluents from the reaction and multiple reaction stages.

The patents and literature cited do not suggest or disclose that unexpected improvements and simplification in the synthesis of N-phenyl-N'-alkyl-p-diphenylamines can be obtained. More specifically, the process of the present invention provides a means for avoiding metal ions in the waste water effluent, improved efficiency of the reaction, and simplification of the procedure.

DISCLOSURE OF THE INVENTION

There is disclosed a process for the reductive alkylation of aromatic nitro-containing compounds with ketones or aldehydes wherein the improvement is characterized in that the reaction is conducted in one-step using a catalyst system that consists of (1) a polymer bound anthranilic acid-Pd complex and (2) a sulfonic acid resin at a temperature from 20°–200° C. and pressure from atmospheric to 35,000 kPa.

There is also disclosed a process wherein the aromatic nitro-containing compound is p-nitrodiphenylamine, the ketone is MIBK, the polymer bound anthranilic acid-palladium complex is a macroreticular styrene/vinylbenzyl chloride/divinylbenzene resin that contains at least 4% crosslinking and from 0.001 to 10% palladium by weight and the sulfonic acid resin is Amberlyst 15.

There is also disclosed a process wherein (1) a nitrodiphenylamine conforming to the following structural formula:

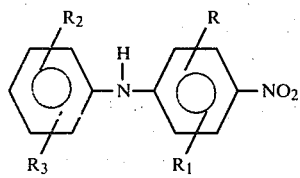
(I)

wherein R and $R_1$ are selected from the group consisting of hydrogen radicals and alkyl radicals of 1 to 9 carbon atoms, $R_2$ and $R_3$ are selected from the group consisting of hydrogen radicals, alkyl radicals of 1 to 9 carbon atoms and alkoxy radicals of 1 to 9 carbon atoms and cycloalkyl radicals of 5 to 6 carbon atoms; is reacted with (2) methylisobutyl ketone to yield a compound of the general structural formula II;

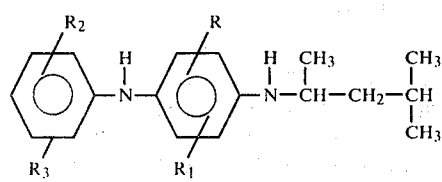
(II)

wherein R, $R_1$, $R_2$, and $R_3$ are defined as above, the improvement characterized in that the reaction is conducted in one step using a catalyst system that consists of (1) polymer bound anthranilic acid-Pd complex and (2) a bound sulfonic acid resin.

The instant invention also contemplates the one stage reductive alkylation of a great many aromatic nitro-containing compounds with either aromatic, aliphatic, or aralkyl ketone and aldehydes. It will be appreciated that the aldehydes and ketones useful in the instant invention may not contain any unsaturation in the alkyl portion.

The process of the present invention can be used with or without solubilizing agents as disclosed in U.S. Pat. No. 4,155,936. The work-up of the final product is described in U.S. Pat. No. 4,155,936.

The catalyst system of the present invention is useful in the preparation of numerous compounds such as:

PRODUCTS

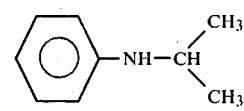

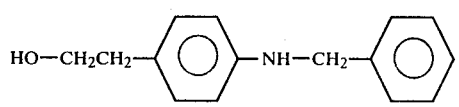

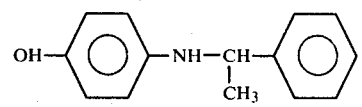

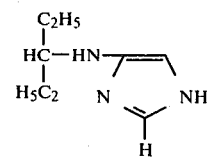

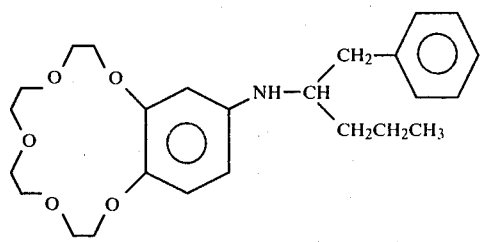

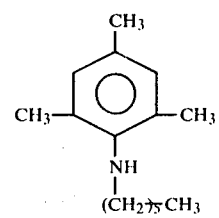

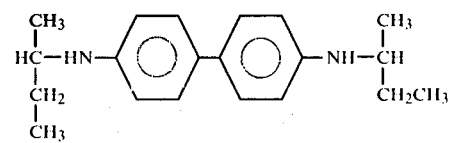

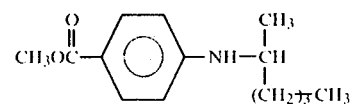

Representative of the aromatic nitro-containing compounds useful in the present invention are:

NITRO COMPOUNDS

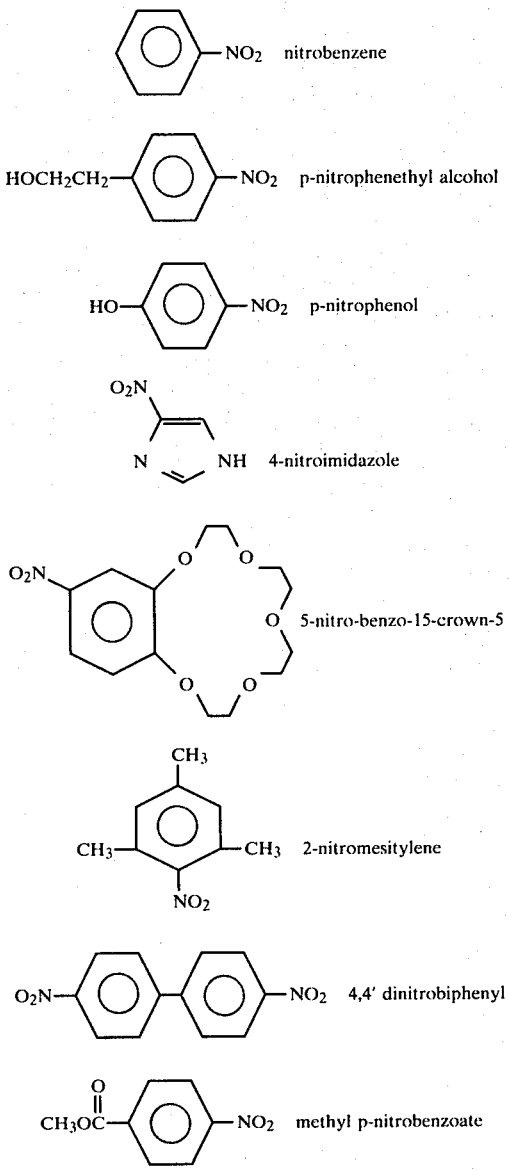

Representative of the ketones or aldehydes in the present invention are:

CARBONYL COMPOUNDS

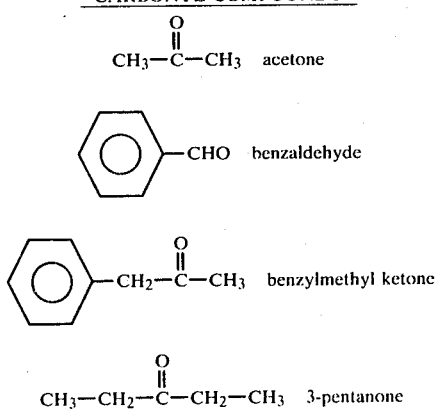

-continued
CARBONYL COMPOUNDS

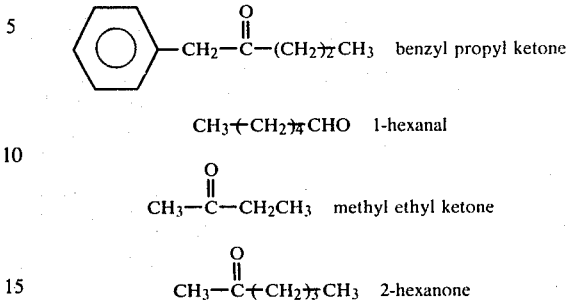

The skilled artisan will appreciate that other strongly acidic resins similar to Amberlyst 15 would be suitable for use in this invention. Amberlyst 15 is a macroreticular, strongly acidic resin known to be useful for heterogeneous acid catalysis of a wide variety of organic reactions in non-aqueous, especially non-polar media. For further information see Rohm and Haas Co. publication dated May 1972, Technical Bulletin; *Amberlyst 15, Synthetic Resin Catalyst.*

Further, the present invention contemplates the use of a resin or polymer that contains both the strongly acidic functionality and the catalytic metal complex.

One skilled in this art will realize that reaction temperature and pressure conditions can be varied according to the exact chemical in use, however, the process of the instant invention can be successfully carried out from 20°–200° C. and from atmospheric pressure to 35,000 kPa. The preferred temperature range is 60°–150° C. with pressure from 350–7000 kPa ($\simeq$50–1000 psi).

The artisan will appreciate that the catalyst system of the present invention would be used in catalytic amounts which will depend upon the millimoles of functionality per gram of resin or polymer. Generally from 0.1–1000 millimoles of palladium bound to the polymer per mole of nitro-containing compound and from 1.0 to 1000 millimole of acid bound to resin per mole of nitro-containing compounds are suitable ratios in the present invention.

BEST MODE FOR CARRYING OUT THE INVENTION

The following examples are intended to illustrate and not to limit the scope of the present invention.

Experimental

1. Typical Preparation of Macroreticular Type Styrene/Vinylbenzyl Chloride/Divinylbenzene Resins A 1-liter three necked flask was fitted with a Teflon stirrer, thermometer well, nitrogen inlet and heated with a Glas-Col mantle. The flask was charged with 300 ml of water and 6.0 g of cellulose 7M (medium viscosity grade from Hercules Rubber Co.). The mixture was agitated vigorously for ten minutes under nitrogen before adding a solution of 150 g of toluene, 82.16 g (0.79 moles) styrene, 20.07 g (0.1316 moles) vinylbenzyl chloride and 80.5 g (0.395 moles) of 50% pure divinylbenzene. Agitation was continued for 10 minutes before the heat was turned on and 1.5 g (0.0091 moles) azobisisobutronitrile was charged. The temperature was gradually raised to 70°–75° over 3–3.5 hours and maintained there for 4 hours. At the end of the polymerization, the suspension was poured into excess cold water, screened, washed and dried in the hood for three days.

Final product weight for the resin was 118.3 grams with a nominal composition of 60/10/30 styrene/vinylbenzyl chloride/divinylbenzene.

50.0 g of the crude resin was washed with acetone before filtering and drying to yield 47.33 g of product. The washed resin was submitted for elemental chlorine analysis with the following results; 2.30% calculated and 1.79% chlorine found.

2. Preparation of Polymer-Bound Macrometicular Anthranilic Acid

A 500 ml 3-neck flask was charged with 25.0 g washed resin prepared above (60/10/30) ($\approx$0.0164 moles chlorine), 5.0 g (0.0365 moles) anthranilic acid, 5.77 g (0.073 moles) pyridine and 250 ml of dimethylformamide (DMF). The mixture was warmed with stirring under nitrogen for 18 hours at 75° C. The mixture was then filtered warm, washed three times with DMF, three times with acetone and then dried in a vacuum oven at 80° C. for three hours to obtain 25.48 g of product resin. Analysis of the reaction showed 0.67% nitrogen.

3. Preparation of Macroreticular Polymer-Bound Palladium Anthranilic Acid Complex A 500 ml 3-neck flask equipped with a mechanical stirrer, thermometer and a condenser was charged with 24.8 g ($\approx$0.012 moles of anthranilic acid resin from 2 above), 0.89 g (0.005 moles), PdCl$_2$ and 250 ml of DMF. The mixture was stirred and warmed to 75° C. under nitrogen for 18 hours. The resin was then filtered off while still warm, washed twice with DMF, twice with DMF/H$_2$O (5/1) and then three times with acetone before drying in an vacuum oven to obtain 25.14 g of orange resin. Analysis showed 0.65% N and 1.71% Pd.

4. Activation of Macroreticular Palladium Anthranilic Acid Complex

A 500 ml 3-neck flask equipped with a magnetic stirring bar and nitrogen inlet was charged with 24.05 g of palladium resin from 3 above ($\approx$0.00386 moles Pd) and 200 ml tetrahydrofuran. After purging with nitrogen, 30 ml (0.015 moles) of 0.5M NaBH$_4$ in diglyme solution was added by means of syringe (all at once). The resin rapidly turned black in color with some gas evolution. After stirring 30 minutes at room temperature, the product was filtered off and washed twice with THF, three times with ethanol and twice with toluene before storing in a clear bottle under toluene for further use.

Use of Prepared Catalyst

5. Reduction of p-nitro diphenylamine: Low Pressure Run.

A 500 ml Parr hydrogenation bottle was charged with 21.4 (0.10 mole) recrystallized p-nitrodiphenylamine, 180 ml ethanol and 3.0 g catalyst from 4 above. After evacuating and repressuring to 350 KPa with hydrogen, heating and shaking were begun. The temperature rose to a maximum of 74° C. and hydrogen uptake ceased $\approx$0.3 moles within one hour. 18.04 g of pure p-aminodiphenylamine was isolated from the filtrate. The catalyst was washed with MIBK and recycled to the next run in which MIBK (180 ml) solvent replaced the ethanol. Again, complete reduction occurs in less than one hour. No Schiff Base formation or ketone reduction was observed.

6. Preparation of N-phenyl-N'-alkyl-p-phenylenediamine using Catalyst from 4 above and Amberlyst 15

Sulfonic Acid Resin (Trademark of Rohm and Haas Co. for a macroreticular sulphonic acid resin containing 4.5 meg of acid per gram of resin).

The specific reaction is:

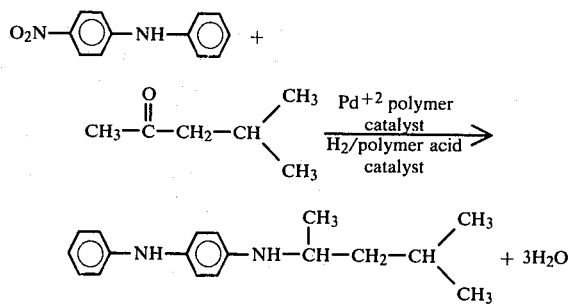

The one-pot reaction takes place in three distinct steps:

(1) Reduction of p-nitrodiphenylamine to p-aminodiphenylamine catalyzed by the Pd$^{+2}$ polymer catalyst.

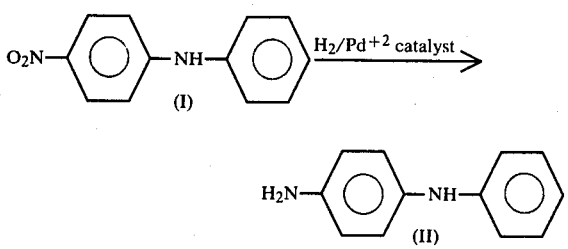

(2) Formation of the Schiff Base of (II) with MIBK catalyzed by the polymeric acid catalyst (Amberlyst 15).

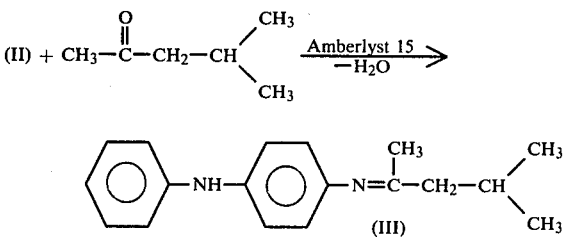

(3) Reduction of the Schiff Base (III) catalyzed by the Pd$^{+2}$ polymer catalyst.

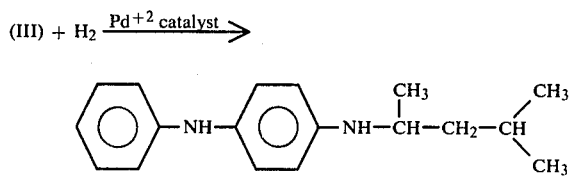

A 500 ml hydrogenation bottle was charged with 21.4 g (0.10 mole) recrystallized p-nitrodiphenylamine, 200 ml methylisobutyl ketone, 3.0 Pd$^{+2}$ polymer catalyst from 4 above and 3.0 g Amberlyst 15 acid catalyst. After evacuating and repressuring to 345 kPa (50 psig) with hydrogen, shaking and heating were begun. The nitro compound was reduced very rapidly; less than 1 hour at 75° C. for uptake of $\approx$0.3 moles of hydrogen. This was followed by a slow reduction of the Schiff Base; 0.1 moles of hydrogen uptake in 5 hours at 70° C.

After cooling and venting, the catalysts were recycled three more times with similar results. The analytical results for the four runs are summarized in Table I.

TABLE I*

| Sample No. | p-Amino-diphenylamine | Schiff Base % | Product %** |
|---|---|---|---|
| 6(A) | 31.9 | 46.0 | 22.2 |
| 6(B) | 12.4 | 46.6 | 41.0 |
| 6(C) | 16.8 | 35.7 | 47.6 |
| 6(D) | 8.4 | 52.5 | 39.1 |

**N—phenyl-N'—alkyl-p-phenylenediamine
*wt % of components by gas chromatographic analysis 7. Preparation of N-phenyl-N'-alkyl-p-phenylenediamine using Anthranilic Acid Palladium$^{+2}$ Polymer Catalyst and Amberlyst 15 High Pressure Run.

A 400 ml capacity Parr autoclave was charged with 21.4 g (0.10 mole) recrystallized p-nitrodiphenylamine, 200 ml methylisobutyl ketone, 5.0 g of a catalyst prepared according to 1 through 4 above with (0.66% Pd) and 5.0 gm Amberlyst 15 resin. The autoclave was sealed and flushed three times with nitrogen. The system was then heated to 70° C. and hydrogen introduced. Pressure was allowed to drop from 6900 kPa (1000 psig) to 6550 kPa (950 psig) and then recharged to 6900 kPa (1000 psig). The stirring rate was approximately 3500 rpm.

After a total reaction time of 7 hrs. (4 hrs. @ 70° C. and 3 hrs. @ 102° C.) no more hydrogen was absorbed. Gas chromatographic analysis indicated:

79.9% N-phenyl-N'-alkyl-p-phenylenediamine
3.6% Schiff Base
11.6% p-aminodiphenylamine Additional experiments were conducted wherein the combined Stage II and III reactions were conducted in a high pressure reactor (6900 kPa, 1000 psig H$_2$). With high pressure reactors the process of the instant invention provides an improved product yield over low pressure reactions.

8. Preparation of 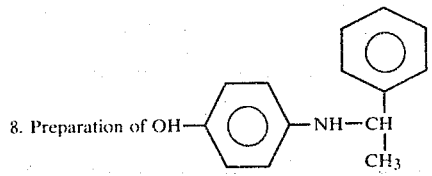

In a 500 ml Parr hydrogenation bottle is charged 0.10 mole of p-nitrophenol, 200 ml MIBK, 5.0 grams of activated catalyst from 1 through 4 above, 5.0 grams Amberlyst 15 resin. The system was flushed with hydrogen, and then pressurized to 350 kPa. Shaking and heating is begun. Reductive alkylation takes place to yield the product.

Results and Discussion

It has been demonstrated by the instant invention that effective macroreticular catalysts can be synthesized from macroreticular resins prepared by simple suspension copolymerization techniques. These resins are easily converted by conventional organic reaction procedures into polymer-bound metal chelate catalysts of high activity. Furthermore, the catalysts have long-term stability on storage, are noncorrosive, nonpyrophoric and appear to be relatively unaffected by water or air.

The ability to synthesize these macroreticular catalysts and resins allows the present invention to utilize their unique properties under a much broader range of conditions than is possible with gel-type resin catalysts or their homogeneous counterparts. A good illustration of this difference in behavior is clearly evident in the catalytic hydrogenation of p-nitrodiphenylamine. The hydrogenation of this compound in ethanol with a gel-type Pd$^{+2}$ polymer-bound catalyst for five hours at 80°–90° C. under 50 psig hydrogenation resulted in only trace reaction. This is in marked contrast to the same reaction carried out under similar conditions with a Pd$^{+2}$ macroreticular polymer-bound catalyst.

The present invention provides in a catalyst system for the production of the antiozonant N-phenyl-N'-alkyl-p-phenylenediamine. It is possible with this catalyst system to combine Stages II (preparation of p-aminodiphenylamine) and III (reductive alkylation of p-aminodiphenylamine with MIBK) into one stage. Such a combination will provide substantial savings through reduced distillation costs and increased yields.

Industrial Applicability

The instant invention combines the current process Stage II and III steps into a single stage. This invention also elminates copper chromite and modified nickel catalysts employed in the current commercial process. Very little, if any, MIBK solvent is reduced to alcohol by the new process. Further, the process of the present invention provides a method which is easily adapted to commercial reductive alkylations of aromatic nitro-containing compounds with aldehydes or ketones.

While certain representative embodiments and details have been shown for the purpose of illustrating the invention, it will be apparent to those skilled in this art that various changes and modifications may be made therein without departing from the scope of the invention.

We claim:

1. A process for the reductive alkylation of aromatic nitro-containing compounds with ketones or aldehydes wherein the improvement is characterized in that the reaction is conducted in one-step using a catalyst system that consists of (1) a polymer bound anthranilic acid-Pd complex and (2) a sulfonic acid resin at a temperature from 20°–200° C. and pressure from atmospheric to 35,000 kPa.

2. A process according to claim 1 wherein the aromatic nitro-containing compound is p-nitrodiphenylamine, the ketone is methylisobutyl ketone, the polymer bound anthranilic acid palladium complex is a macroreticular styrene/vinylbenzyl chloride/divinylbenzene resin that contains at least 4% crosslinking and from 0.001 to 10% palladium. by weight and the sulfonic acid resin is Amberlyst 15.

3. A process according to claim 1 wherein the reaction is conducted from 60°–150° C. and at a pressure of 350–7000 kPa.

4. A process wherein (1) a nitrodiphenylamine conforming to the following structural formula:

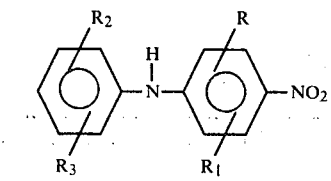

(I)

wherein R and $R_1$ are selected from the group consisting of hydrogen radicals and alkyl radicals of 1 to 9 carbon atoms, $R_2$ and $R_3$ are selected from the group consisting of hydrogen radicals, alkyl radicals of 1 to 9 carbon atoms and alkoxy radicals of 1 to 9 carbon atoms and cycloalkyl radicals of 5 to 6 carbon atoms; is reacted with (2) methylisobutyl ketone to yield in a compound of the general structural formula II;

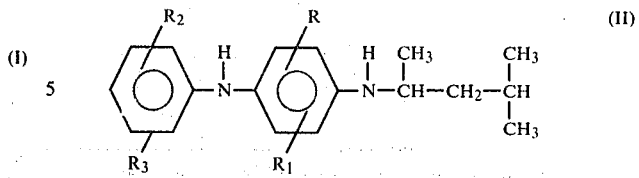

(II)

wherein R, $R_1$, $R_2$, and $R_3$ are defined as above, the improvement characterized in that the reaction is conducted in one step using a catalyst system that consists of (1) polymer bound anthranilic acid-Pd complex and (2) a bound sulfonic acid resin.

5. A process according to claim 4 wherein the aromatic nitro-containing compound is p-nitrodiphenylamine, the ketone is methylisobutyl ketone, the polymer bound anthranilic acid-Pd complex is a 60/10/30 styrene/vinylbenzyl chloride/divinylbenzene resin that contains from 0.001–10% palladium by weight and the sulfonic acid resin is Amberlyst 15.

6. A process according to claim 4 wherein the reaction is conducted from 60°–150° C. and at a pressure of 350–7000 kPa.

* * * * *